United States Patent [19]
Suzuki et al.

[11] 4,383,729
[45] May 17, 1983

[54] LIGHT TRANSMITTING SYSTEM COMPRISING BEAM DIVIDING AND COMPOSITING MEANS

[75] Inventors: Masane Suzuki; Motonori Kanaya, both of Omiya, Japan

[73] Assignee: Fuji Photo Optical Co., Ltd., Omiya, Japan

[21] Appl. No.: 197,823

[22] Filed: Oct. 17, 1980

[30] Foreign Application Priority Data

Nov. 12, 1979 [JP] Japan .................................. 54-146324

[51] Int. Cl.³ .............................................. G02B 5/16
[52] U.S. Cl. .............................. 350/96.10; 350/96.26; 350/174
[58] Field of Search ............... 350/96.10, 96.18, 96.26, 350/167, 169, 171, 173, 174

[56] References Cited
U.S. PATENT DOCUMENTS

| | | | |
|---|---|---|---|
| 3,534,158 | 10/1970 | Eilenberger | 350/173 UX |
| 3,962,702 | 6/1976 | Kriege | 350/96.10 X |
| 4,093,964 | 6/1978 | Aughton | 350/174 X |
| 4,156,555 | 5/1979 | McMahon | 350/167 X |
| 4,208,094 | 6/1980 | Tomlinson et al. | 350/96.18 X |

OTHER PUBLICATIONS

Marks, *Optical Multiplexor for Apertured Document Reading*, IBM Tech. Discl. Bulletin, vol. 13, No. 10, Mar. 1971, p. 3006.

*Primary Examiner*—Paul L. Gensler

[57] ABSTRACT

A laser beam emitted from a laser is divided into a plurality of beams and the divided beams are introduced into respective fiberoptics. Each beam is transmitted through the corresponding fiberoptic and projected from the exit face of the fiberoptic, where the beams are synthesized to form a light spot. The affected part of a patient to be treated is exposed to the light spot.

5 Claims, 7 Drawing Figures

LIGHT TRANSMITTING SYSTEM COMPRISING BEAM DIVIDING AND COMPOSITING MEANS

BACKGROUND OF THE INVENTION

1. Field of the Invention

This invention relates to a light transmitting system, and more particularly to a light transmitting system using optical fibers suitable for transmitting a light beam having a high energy density such as a laser beam.

2. Description of the Prior Art

Recently, material processing techniques utilizing light energy have come into practical use. Such material processing techniques are advantageous in that the material can be processed without mechanical contact, and that it is relatively easy to obtain access to the part of the material to be processed even when the part is disposed in a narrow space of complicated shape.

The concept of light energy processing is employed for example in such medical instruments used with an endoscope as the laser scalpel and the laser coagulator.

Generally, the instrument for carrying out the light energy processing comprises a light source such as a laser and a light transmitting system for guiding a light beam emitted from the light source to the part of the material to be processed. Ordinarily, the light transmitting system comprises a fiberoptic bundle having a light entrance face and a light exit face. The light beam emitted from the light source is caused to impinge on the entire area of the light entrance face of the fiberoptic bundle and is transmitted through each optical fiber of the bundle to emanate from the exit face thereof to strike the material to be processed. The light beam employed in light energy processing is generally a laser beam having a high energy density such as a $CO_2$ laser, a YAG laser or an Ar laser.

The conventional light transmitting system in which the laser beam emitted from the laser is caused to impinge on the entire area of the entrance face of the fiberoptic bundle gives rise to some problems when the light output power of the laser is increased. When the light output power of the laser is increased beyond a certain level the transmission efficiency of the light transmitting system is substantially lowered; that is, a substantial amount of the light energy is lost in the space between the optical fibers of the bundle, this space being occupied by adhesive for binding the optical fibers together to form the bundle and not contributing to the transmission of the light energy. Further, the adhesive between the optical fibers is deteriorated by the light energy and the deteriorated adhesive damages and contaminates the entrance face of the bundle. Especially, when the optical fibers used are of the core/cladding type, the energy loss at the light entrance face may be as high as 70 to 80% since the cladding does not contribute to light energy transmission.

These problems can be overcome by transmitting the light energy through a single optical fiber having a relatively large outer diameter of, for example, 300–400μ. However, the optical fiber of such a large diameter has poor flexibility, whereas it is desirable for the light transmitting system to have high flexibility at least at the portion near the light exit face so that the light beam emanating therefrom can be easily directed in the required direction. Especially when the light energy processing instrument is used with an endoscope, the light transmitting system should be flexible enough to be bendable along with the endoscope. For example, an endoscope for the stomach or the duodenum may sometimes be bent to form an arc having a radius of curvature of about 15 mm.

In order to obtain such a high flexibility with a single fiber, the diameter of the fiber must be as small as 150μ (about 100μ at its core). However, a thin optical fiber even a heat resistant fiber having a quartz core, would be damaged by heat if a laser beam of high energy density should be transmitted therethrough.

Thus there has been a great demand for a light transmitting system which has high flexibility and can transmit light having high energy density without substantial loss of the light energy.

In the medical use of light energy processing, the affected part is exposed to a light spot. It is preferred that the energy level be uniform over the entire area of the light spot so that a uniform effect can be obtained within the spot. If the light energy is not uniformly distributed throughout the light spot, the area of the affected part subjected to the lower energy will not be properly treated. Accordingly, the light spot must be moved so that the entire area of the affected part is exposed to the light of the higher energy level. However, provision of a mechanism for moving the light spot would adversely affect the flexbility of the entire endoscope assembly. If the output power of the laser is increased to raise the energy level of the lower energy area up to a level high enough for the treatment, then the area of the affected part subjected to the higher energy level might possibly be damaged.

SUMMARY OF THE INVENTION

In light of the foregoing observation and description, the primary object of the present invention is to provide a light transmitting system which can transmit light having a high energy density with high transmission efficiency and has high flexibility.

Another object of the present invention is to provide a light transmitting system which can produce a light spot having a uniform distribution of light energy over the entire area thereof.

The light transmitting system of the present invention comprises a light dividing means for dividing a light beam emitted from a light source into a plurality of light beams, and a like number of optical fibers each of which has its entrance face disposed in the optical path of one of the divided light beams.

In the light transmitting system of the present invention, the light beam emitted from the light source is divided into a plurality of light beams and each of the beams is introduced into the entrance face of an associated optical fiber. Accordingly, no light energy is lost in the space between the entrance faces of the optical fiber and, moreover, the adhesive in the space is not adversely affected by the light energy.

As the optical fiber, it is possible to use not only a core/cladding type optical fiber but also a graded optical fiber having a refraction gradient from the center of the core toward the periphery thereof.

As the beam dividing means, there can be used a beam splitter, a plurality of semi-transparent mirror faces arranged along the optical path of the beam emitted from the light source, or a combination of a lens system for converting the light beam from the light source into a wider coherent light beam and a plurality at fly-eye lenses which are disposed in the optical path of the widened beam and concentrate it on a plurality of points. Other like means are also employable.

Further, the light transmitting system of the present invention can be applied to various applications other than laser medical treatment instruments. For example, it can be used for holography using an endoscope or for a material processing system for processing a material with high energy density light.

DESCRIPTION OF THE PREFERRED EMBODIMENT

Figure 1:
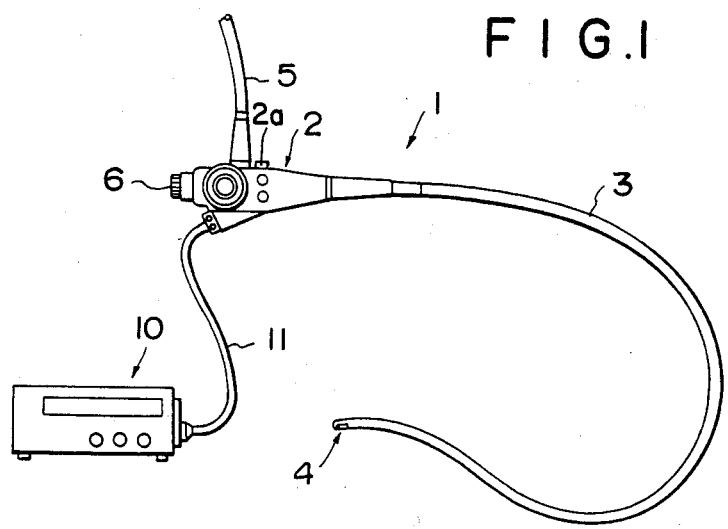
FIG. 1 shows an endoscope incorporating a light energy medical treatment instrument employing a light transmitting system in accordance with an embodiment of the present invention.

FIG. 1 shows an endoscope incorporating a laser medical treatment instrument having a light transmitting system in accordance with an embodiment of the present invention.

The endoscope 1 comprises an operating portion 2, a flexible tube portion 3 having a viewing window 4 at the free end thereof, light guiding tube portion 5 for introducing illuminating light and an eyepiece portion 6.

The beam transmitting tube 11 of the laser medical treatment instrument 10 is inserted into the flexible tube portion 3 to reach the viewing window 4.

Figure 2:
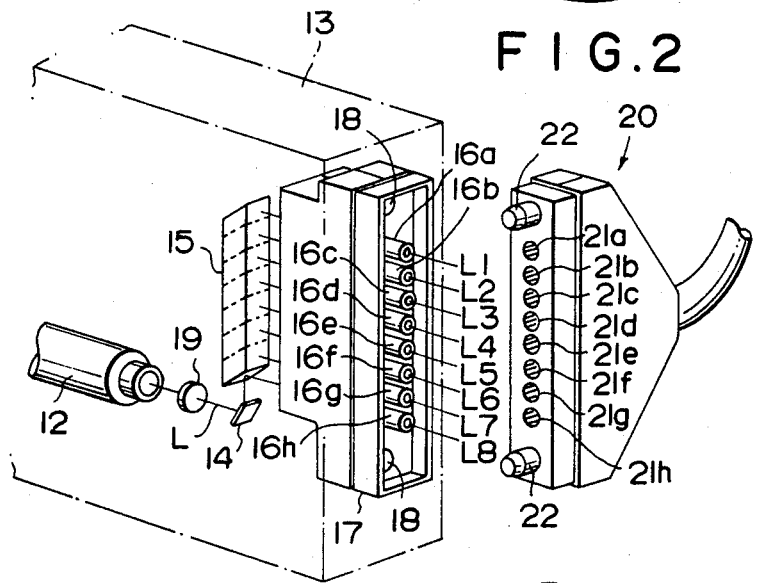
FIG. 2 is an enlarged view of a part of the light transmitting system employed in the endoscope of FIG. 1.

As shown in FIG. 2, the laser medical treating instrument 10 has a laser 12 secured within a housing 13. A laser beam L emitted from the laser 12 is reflected by a mirror 14 and introduced into a beam dividing means 15 to be divided into a plurality of beams. In this particular embodiment, the beam dividing means 15 has seven semi-transparent mirror faces and a single reflecting mirror face (not shown in detail) and thus divides the laser beam into eight light beams $L_1$-$L_8$. The light beams $L_1$-$L_8$ are introduced into eight rigid guiding tubes 16a-16h held by a female connector 17 which is secured to the housing 13.

A male connector 20 is mounted on the light entrance end of the beam transmitting tube 11. The beam transmitting tube 11 comprises eight flexible optical fibers bound together to form a bundle.

The light entrance end portion of the bundle is unbound into eight separate optical fibers and the individual optical fibers are respectively inserted into eight holes 21a-21h provided in the male connector 20. When the male connector 20 is fit into the female connector 17, said rigid light guiding tubes 16a-16h are received in the holes 21a-21h, the male connector 20 being located with respect to the female connector 17 so that the rigid light guiding tubes 16a-16h and the holes 21a-21h are accurately aligned with each other by means of a pair of locating pins 22 provided on the male connector 20 and a pair of locating holes 18 provided in the female connector 17.

Said divided light beams $L_1$-$L_8$ are thus introduced into the individual optical fibers and emanate from the light exit faces thereof. In the light exit portion of the light transmitting tube 11, the individual optical fibers are bundled together. Accordingly, the divided laser beams $L_1$-$L_8$ are synthesized again to form a single light spot. The light spot is projected from the viewing window 4 of the endoscope to expose the affected part of a patient to be treated.

By appropriately selecting the transmissivity (or reflectivity), the inclination with respect to the optical axis of the beam L, or the like of each semi-transparent mirror face, the divided laser beams $L_1$-$L_8$ can be made to have energy densities equal to each other.

Figure 3:
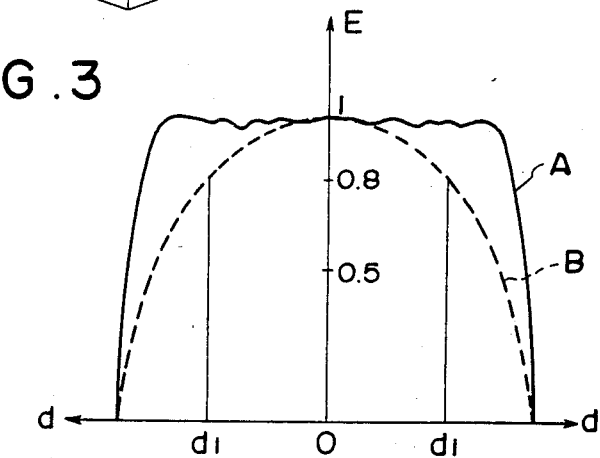
FIG. 3 graphically shows the energy distribution in a light spot formed by the light transmitting system of the present invention, the solid line A being the energy distribution curve in a light spot formed by the light transmitting system of the present invention and the dotted line B being the same in a light spot formed by the conventional light transmitting system.

Thereby, the light spot formed can have a uniform distribution of light energy over the entire area thereof. FIG. 3 graphically shows the energy distribution within the spot. In FIG. 3, ordinate and abscissa represent the specific energy intensity when the energy intensity at the center of the spot is assumed to be 1 and the distance from the center of the spot, respectively, the solid line A being the energy distribution curve of the light spot formed by the light transmitting system in accordance with the present invention and dotted line B being the same of the light spot formed by the conventional light transmitting system.

As can be seen from the dotted line B, in the light spot formed by the conventional light transmitting system, the energy intensity decreases substantially toward the periphery. Accordingly, assuming that a specific energy intensity of 0.8 or more is required for the medical treatment concerned, satisfactory treating effect can be obtained only in the area defined by a radius of $d_1$ from the center of the spot. Therefore the light spot must be moved so that the entire area of the affected part to be treated is exposed to the light in said area of the spot since the area is substantially smaller than the entire area of the light spot. This is very troublesome, and makes the endoscope very complicated. Furthermore, it is very difficult to move the light spot in a finely controlled manner as the flexibility of the endoscope is insufficient.

If the output power of the laser is increased to raise the energy intensity of the peripheral area of the light spot up to the level required for the relevant treatment, then the energy intensity of the area near the center of the light spot is raised too high so that the tissue of the exposed part may possibly be damaged.

On the contrary, in the light spot formed by the light transmitting system of the present invention, the energy intensity is substantially uniformly distributed over the entire area thereof as can be seen from the solid line A. Therefore, substantially uniform treating effect can be obtained over the entire area of the affected part exposed to the light spot.

Referring to FIG. 2 again, an optical element such as a filter or a shutter may be inserted in the optical path of the beam L as indicated at 19 in order to adjust the intensity of the beam transmitted to the beam dividing means 15, to completely block the beam, or to carry out pulse modulation of the beam.

If required, an optical element may be disposed between the beam dividing means 15 and each rigid light guiding tube 16a–16h or in each rigid light guiding tube 16a–16h for separately controlling the intensity of the divided beams $L_1$–$L_8$. Although the rigid light guiding tubes 16a–16h are preferred to be optical fibers, they may be hollow tubes.

When using the light transmitting system of the present invention together with an endoscope as in the embodiment of FIGS. 1 and 2, the beam transmitting tube 11 preferably comprises 5–10 optical fibers having an outer diameter of 150$\mu$ (100$\mu$ at the core thereof). By this arrangement, each optical fiber will be able to transmit a light beam having a relatively high energy density and the light transmitting tube 11 will be flexible enough to be bent to form an arc having a radius of curvature of about 10 mm.

Again referring to FIG. 1, the beam transmitting tube 11 may be inserted into a passage way for forceps which is normally provided in the flexible tube portion 3 of the endoscope 1 or may be inserted into a passage way separately provided in the endoscope 1. In the latter case, the beam transmitting tube 11 may be divided into a light exit side portion and a light entrance side portion. The light exit side portion is permanently placed in the passage way, while the light entrance side portion is detachably mounted on the light exit side portion through a connector. The light exit side portion should have a flexible coating while the light entrance side portion may have a coating which serves to protect the fiberoptics.

Treatment is conducted by exposing the affected part to be treated to a laser beam while observing the affected part from the eyepiece portion 6, the laser beam being adjusted in advance in its intensity by controlling the output power of the laser 12. If required, the laser beam may be modulated. It is preferred that an on-off switch be provided near the operating portion 2 as indicated at 2a for turning on and off the laser beam and also for safety. By controlling the laser 12 or by providing appropriate optical elements at the ends of the light transmitting tube 11, the diameter of the light spot can be changed in accordance with the condition of the affected part.

Figure 4:
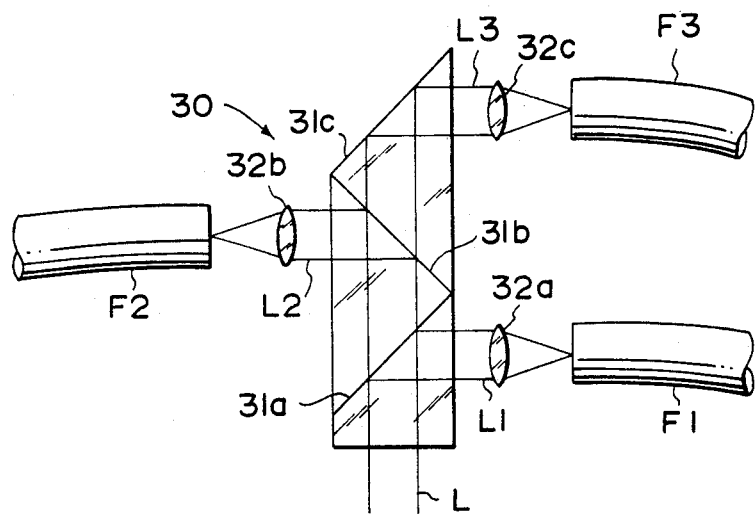
FIGS. 4 to 6 respectively show various beam dividing means which can be employed in the present invention.
Figure 5:
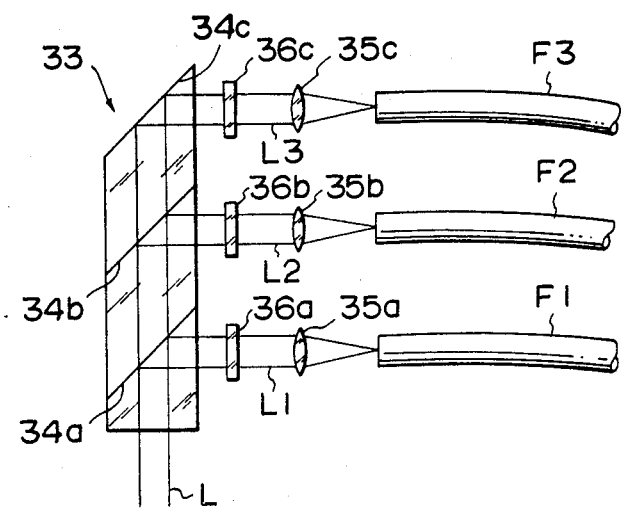
Figure 6:
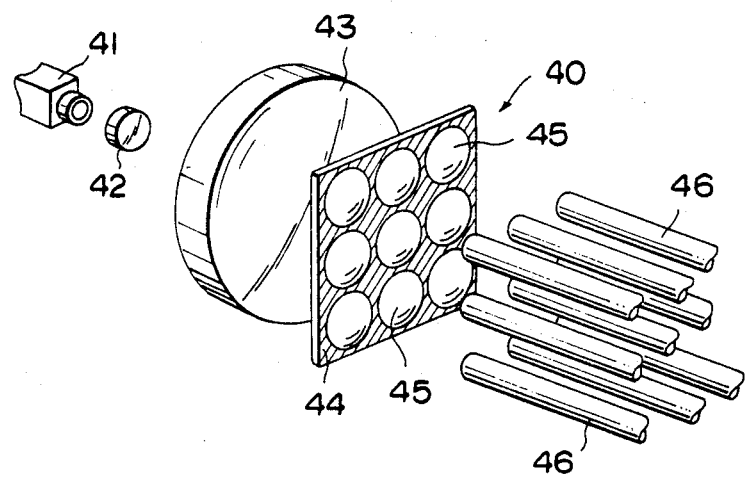

FIGS. 4 to 6 show different beam dividing means which can be employed in the present invention.

The beam dividing means 30 shown in FIG. 4 consists of three prisms and includes two semi-transparent mirror faces 31a and 31b, and mirror face 31c. The first semi-transparent mirror face 31a is disposed in the optical path of the beam L emitted from the light source (not shown in FIG. 4) inclined with respect thereto. The first semi-transparent mirror face 31a reflects a part of the beam L and transmits the remaining part therethrough. The reflected part $L_1$ of the beam L is converged by a converging lens 32a and introduced into an optical fiber $F_1$. The second semi-transparent mirror face 31b is inclined with respect to the optical path of the beam passing through the first semi-transparent mirror face 31a in the opposite direction and reflects a part of the beam passing through the first semi-transparent mirror face 31a in the direction opposite to the direction of the beam $L_1$ as indicated at $L_2$. Further, the second semi-transparent mirror face 31b transmits therethrough the remaining part of the beam passing through the first semi-transparent mirror face 31a. The reflected part $L_2$ is converged by a converging lens 32b and introduced into an optical fiber $F_2$. The remaining part transmitted through the second semi-transparent mirror face 31b is reflected by the mirror face 31c in the same direction as the beam $L_1$ as indicated at $L_3$ and introduced into an optical fiber $F_3$ passing through a converging lens 32c. It is preferred that the reflectivities of the first and second semi-transparent mirror faces 31a and 31b be about 30% and 50% respectively, so that the intensities of the beams $L_1$–$L_3$ are substantial equal to each other.

The beam dividing means 33 shown in FIG. 5 includes two semi-transparent mirror faces 34a, 34b and a mirror face 34c. All the mirror faces 34a, 34b and 34c are inclined with respect to the optical axis of the beam L in the same direction. As in the beam dividing means 30 of FIG. 4, the divided beams $L_1$, $L_2$ and $L_3$ are converged by converging lenses 35a–35c and introduced into optical fibers $F_1$–$F_3$, respectively.

In the optical paths of the divided beams $L_1$–$L_3$ are inserted ND (neutral density) filters 36a–36c, respectively, whereby the intensity of the beams $L_1$–$L_3$ can be separately adjusted. The ND filters 36a–36c may be made exchangeable so that an ND filter of a suitable density can be placed in the optical path of each beam in accordance with the required intensity of the beam. Otherwise, each ND filter may comprise a plurality of sections having continuously changing densities. In this case, the intensity of the beams $L_1$–$L_3$ can be adjusted by selecting the section to be placed in the optical path thereof.

In the beam dividing means 40 shown in FIG. 6, a light beam emitted from a light source 41 is diverged to a predetermined extent by a diverging lens 42, and the diverged light beam is converted into a coherent light bundle by a lens 43. In the optical path of the coherent light bundle is disposed a plate element 44 perpendicularly to the optical axis of the light bundle. The plate element 44 is provided with a plurality of fly-eye lenses 45. The light bundle is concentrated on a plurality of points by the fly-eye lenses 45 on which points respective light entrance faces of optical fibers 46 are positioned.

In this beam dividing means 40, the light energy impinging on the area of the plate element 44 where no fly-eye lenses 45 are provided is lost. Nevertheless, the light energy loss in the beam dividing means 40 is substantially small, especially in the peripheral area of the light beam, compared with that of the conventional light transmitting system.

In the light transmitting system of the present invention, the light beams emanating from the exit faces of the optical fibers may be combined together to form a single light spot or may be separately used.

Figure 7:
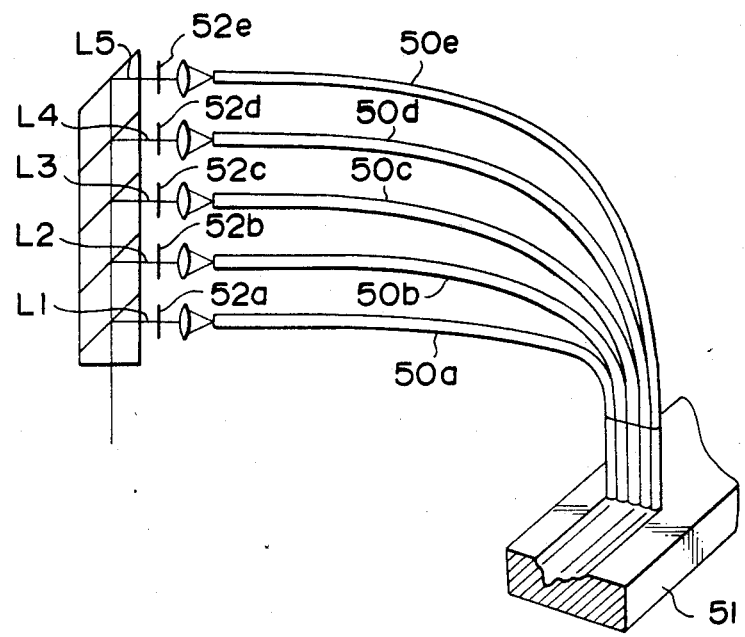
FIG. 7 schematically shows an example of a material processing system employing the light transmitting system of the present invention.

In another embodiment of the present invention shown in FIG. 7, five optical fibers 50a–50e extend from the entrance face to the exit face thereof separately from each other and are tied together side by side. The light beams $L_1$–$L_5$ are used to form recesses in different parts of material 51 to be processed. By controlling the intensity of each beam $L_1$–$L_5$ by means of controlling elements 52a–52e one disposed in the optical path of each beam $L_1$–$L_5$, the depth of the recess formed by the beam can be changed as shown in FIG. 7.

When the light transmitting system of the present invention in which the optical fibers are not bound at least at the exit end portion to a medical treatment device for stimulating acupuncture points spots of a human body (See for example the U.S. patent application Ser. No. 85,799, now abandoned, filed by this applicant.), a plurality of acupuncture points can be simultaneously stimulated, whereby higher treating effect can be obtained.

We claim:

1. A light transmitting system for transmitting a laser beam of high energy concentration from a single laser beam source, comprising:

a beam dividing means for dividing a light beam from a laser beam source into a plurality of light beams of equal intensity and emitting the divided light beams in a predetermined arrangement, and a beam guiding means consisting of a plurality of flexible optical fibers each of a diameter of about 150μ having a beam entrance end in which one end of the optical fibers is separated into a plurality of ends arranged in an arrangement corresponding to said predetermined arrangement to receive said plurality of light beams respectively, and a beam exit end in which the other end of the optical fibers is bound into a bundle to make the light beams emanating from the optical fibers form a composite light beam.

2. A light transmitting system as defined in claim 1 in which a control means for controlling the amount of light entering each said optical fiber is provided in the optical path of each divided beam.

3. A light transmitting system as defined in claim 1, in which each of said optical fibers has a core having a diameter of about 100μ.

4. A light transmitting system as defined in claim 1, in which said beam dividing means comprises a plurality of semi-transparent mirror faces arranged in the optical path of the light beam emitted from the light source and inclined with respect thereto.

5. A light transmitting system as defined in claim 1, in which said beam dividing means comprises an optical system for converting the light beam emitted from the laser source into a coherent light bundle having a predetermined diameter, and a plurality of converging optical systems positioned behind said optical system in a plane perpendicular to the coherent light bundle.

* * * * *